US009364642B2

(12) United States Patent
Sina

(10) Patent No.: US 9,364,642 B2
(45) Date of Patent: Jun. 14, 2016

(54) BALLOON CATHETER SYSTEMS AND METHODS FOR BYPASSING AN OCCLUSION IN A BLOOD VESSEL

(71) Applicant: Invatec S.p.A., Roncadelle (IT)

(72) Inventor: Achille Sina, Sarezzo (IT)

(73) Assignee: Invatec S.P.A., Roncadelle, BS (IT)

( * ) Notice: Subject to any disclaimer, the term of this patent is extended or adjusted under 35 U.S.C. 154(b) by 491 days.

(21) Appl. No.: 13/966,920

(22) Filed: Aug. 14, 2013

(65) Prior Publication Data

US 2015/0051632 A1  Feb. 19, 2015

(51) Int. Cl.
*A61M 25/10*  (2013.01)
*A61M 25/01*  (2006.01)
*A61M 29/02*  (2006.01)

(52) U.S. Cl.
CPC ....... *A61M 25/1011* (2013.01); *A61M 25/0155* (2013.01); *A61M 25/0194* (2013.01); *A61M 25/1002* (2013.01); *A61M 25/104* (2013.01); *A61M 29/02* (2013.01); *A61M 2025/0197* (2013.01); *A61M 2025/1013* (2013.01); *A61M 2025/1015* (2013.01)

(58) Field of Classification Search
CPC ............... A61M 25/1011; A61M 25/0194; A61M 25/0155; A61M 29/02; A61M 25/1002; A61M 25/104; A61M 2025/1013; A61M 2025/1015; A61M 2025/0197
See application file for complete search history.

(56) References Cited

U.S. PATENT DOCUMENTS

| 4,552,554 | A | 11/1985 | Gould et al. |
| 4,774,949 | A | 10/1988 | Fogarty |
| 4,983,165 | A | 1/1991 | Loiterman |
| 5,383,856 | A * | 1/1995 | Bersin ................. A61M 25/104 606/194 |
| 5,505,702 | A | 4/1996 | Arney |
| 5,645,529 | A | 7/1997 | Fagan et al. |
| 5,707,389 | A | 1/1998 | Louw et al. |
| 5,830,222 | A | 11/1998 | Makower |
| 5,916,194 | A | 6/1999 | Jacobsen et al. |
| 5,947,994 | A | 9/1999 | Louw et al. |
| 6,068,638 | A | 5/2000 | Makower |
| 6,071,292 | A | 6/2000 | Makower et al. |

(Continued)

FOREIGN PATENT DOCUMENTS

| EP | 1683541 | 7/2006 |
| EP | 1765193 | 10/2012 |

(Continued)

OTHER PUBLICATIONS

Karkos et al. "Subintimal Recanalization of the Femoropopliteal Segment to Promote Healing of an Ulcerated Below-Knee Amputation Stump" J Endovasc Ther 2006;13:420-423.

(Continued)

*Primary Examiner* — Julian W Woo

(57) ABSTRACT

A catheter for subintimally bypassing an occlusion in a vessel includes a catheter shaft including a guidewire lumen disposed therethrough and having a shaft longitudinal axis, at least two balloons coupled to an exterior of the catheter shaft such that longitudinal axes of the balloons are in a common plane with the shaft longitudinal axis when uninflated and with no external forces on the catheter. The balloons are configured such that when the catheter is disposed in the subintima of a vessel and the balloons are inflated, a tip of the catheter shaft is oriented towards a true lumen of the vessel distal of the occlusion.

25 Claims, 10 Drawing Sheets

(56) References Cited

U.S. PATENT DOCUMENTS

| | | | |
|---|---|---|---|
| 6,081,738 A | 6/2000 | Hinohara et al. |
| 6,159,225 A | 12/2000 | Makower |
| 6,178,968 B1 | 1/2001 | Louw et al. |
| 6,190,353 B1 | 2/2001 | Makower et al. |
| 6,203,524 B1 | 3/2001 | Burney et al. |
| 6,217,527 B1 | 4/2001 | Selmon et al. |
| 6,221,049 B1 | 4/2001 | Selmon et al. |
| 6,231,546 B1 | 5/2001 | Milo et al. |
| 6,231,563 B1 | 5/2001 | White et al. |
| 6,231,587 B1 | 5/2001 | Makower et al. |
| 6,235,000 B1 | 5/2001 | Milo et al. |
| 6,283,983 B1 | 9/2001 | Makower et al. |
| 6,287,317 B1 | 9/2001 | Makower et al. |
| 6,302,875 B1 | 10/2001 | Makower et al. |
| 6,375,615 B1 | 4/2002 | Makower et al. |
| 6,379,319 B1 | 4/2002 | Garibotto et al. |
| 6,432,127 B1 | 8/2002 | Kim et al. |
| 6,447,477 B2 | 9/2002 | Burney et al. |
| 6,458,098 B1 | 10/2002 | Kanesaka |
| 6,508,824 B1 | 1/2003 | Flaherty et al. |
| 6,511,458 B2 | 1/2003 | Milo et al. |
| 6,514,217 B1 | 2/2003 | Selmon et al. |
| 6,544,230 B1 | 4/2003 | Flaherty et al. |
| 6,579,311 B1 | 6/2003 | Makower |
| 6,602,241 B2 | 8/2003 | Makower et al. |
| 6,655,386 B1 | 12/2003 | Makower et al. |
| 6,669,709 B1 | 12/2003 | Cohn et al. |
| 6,709,444 B1 | 3/2004 | Makower et al. |
| 6,719,725 B2 | 4/2004 | Milo et al. |
| 6,726,677 B1 | 4/2004 | Makower et al. |
| 6,746,464 B1 | 6/2004 | Makower et al. |
| 7,004,173 B2 | 2/2006 | Sparks et al. |
| 7,059,330 B1 | 6/2006 | Makower et al. |
| 7,066,914 B2 | 6/2006 | Andersen |
| 7,141,041 B2 | 11/2006 | Seward |
| 7,179,270 B2 | 2/2007 | Makower et al. |
| 7,316,655 B2 | 1/2008 | Garibotto et al. |
| 7,357,794 B2 | 4/2008 | Makower et al. |
| 7,534,223 B2 | 5/2009 | Boutilette et al. |
| 7,606,615 B2 | 10/2009 | Makower et al. |
| 7,637,870 B2 | 12/2009 | Flaherty et al. |
| 7,729,738 B2 | 6/2010 | Flaherty et al. |
| 7,833,197 B2 | 11/2010 | Boutilette et al. |
| 7,854,727 B2 | 12/2010 | Belsley |
| RE42,049 E | 1/2011 | Schroeder et al. |
| 7,878,986 B2 | 2/2011 | Jen et al. |
| 7,938,819 B2* | 5/2011 | Kugler ................... A61B 17/22 606/159 |
| 8,083,727 B2 | 12/2011 | Kugler et al. |
| 8,172,863 B2 | 5/2012 | Robinson et al. |
| 8,202,246 B2 | 6/2012 | Kugler et al. |
| 8,221,357 B2 | 7/2012 | Boutillette |
| 8,226,566 B2 | 7/2012 | Nita |
| 8,241,311 B2 | 8/2012 | Ward et al. |
| 8,257,382 B2 | 9/2012 | Rottenberg et al. |
| 8,323,261 B2 | 12/2012 | Kugler et al. |
| 8,337,425 B2 | 12/2012 | Olson et al. |
| 8,388,876 B2 | 3/2013 | Boutilette et al. |
| 8,460,254 B2 | 6/2013 | Belsley |
| 8,486,022 B2 | 7/2013 | Ludwig et al. |
| 8,496,679 B2 | 7/2013 | Robinson et al. |
| 8,512,310 B2 | 8/2013 | Kugler et al. |
| 8,535,245 B2 | 9/2013 | Jen et al. |
| 8,556,857 B2 | 10/2013 | Boutillette |
| 9,174,032 B2* | 11/2015 | Zhou ..................... A61M 25/09 |
| 2001/0000041 A1 | 3/2001 | Selmon et al. |
| 2001/0034547 A1 | 10/2001 | Hall et al. |
| 2002/0072706 A1 | 6/2002 | Hiblar et al. |
| 2004/0167554 A1 | 8/2004 | Simpson et al. |
| 2005/0021003 A1 | 1/2005 | Caso et al. |
| 2005/0171478 A1 | 8/2005 | Selmon et al. |
| 2006/0094930 A1 | 5/2006 | Sparks et al. |
| 2006/0276749 A1 | 12/2006 | Selmon et al. |
| 2008/0125748 A1 | 5/2008 | Patel |
| 2008/0147000 A1 | 6/2008 | Seibel et al. |
| 2009/0124899 A1 | 5/2009 | Jacobs et al. |
| 2009/0264826 A1* | 10/2009 | Thompson .......... A61B 17/3207 604/164.13 |
| 2010/0063534 A1 | 3/2010 | Kugler et al. |
| 2010/0069945 A1* | 3/2010 | Olson .................... A61B 17/11 606/185 |
| 2011/0144677 A1* | 6/2011 | Ward ............. A61B 17/320783 606/170 |
| 2011/0144742 A1 | 6/2011 | Madrid et al. |
| 2011/0276079 A1 | 11/2011 | Kugler et al. |
| 2012/0095485 A1 | 4/2012 | Cully et al. |
| 2012/0283571 A1 | 11/2012 | Nita |
| 2012/0283761 A1 | 11/2012 | Rosenthal et al. |
| 2012/0323251 A1 | 12/2012 | Kugler et al. |
| 2012/0323269 A1* | 12/2012 | Rottenberg ............ A61B 17/02 606/194 |
| 2013/0006167 A1 | 1/2013 | Alvarez |
| 2013/0006173 A1 | 1/2013 | Alvarez et al. |
| 2013/0006282 A1 | 1/2013 | Wilkinson |
| 2013/0072957 A1 | 3/2013 | Anderson |
| 2013/0103070 A1 | 4/2013 | Kugler et al. |
| 2013/0116622 A1 | 5/2013 | Takagi |
| 2013/0150880 A1* | 6/2013 | Anderson .......... A61B 17/3207 606/194 |
| 2013/0158519 A1 | 6/2013 | Boutilette et al. |
| 2013/0245430 A1 | 9/2013 | Selmon et al. |
| 2013/0296907 A1 | 11/2013 | Robinson et al. |
| 2013/0304108 A1 | 11/2013 | Weber et al. |
| 2013/0310868 A1 | 11/2013 | Kugler et al. |
| 2013/0317528 A1 | 11/2013 | Anderson et al. |
| 2014/0277053 A1* | 9/2014 | Wang ................ A61M 25/0194 606/185 |
| 2015/0032142 A1* | 1/2015 | Silvestro ............ A61B 17/3415 606/185 |

FOREIGN PATENT DOCUMENTS

| | | |
|---|---|---|
| GB | 2502956 | 12/2013 |
| WO | WO2008/120209 | 10/2008 |
| WO | WO2009100129 | 8/2009 |
| WO | WO2009/144561 | 12/2009 |
| WO | WO2013003757 | 1/2013 |
| WO | WO2013164825 | 11/2013 |

OTHER PUBLICATIONS

Glasby et al. "Subintimal Angioplasty" Review, pp. 12-16, 2008.
Bolia, A. "Subintimial Angioplasty, the Way Forward" Acta Chir Belg, 2004, 104, 547-554.
Bolia A. "Subintimal Angioplasty, Tips and Technique: How Long Can You Go?" Date unknown.
Shin et al. "Limitations of the Outback LTD Re-Entry Device in Femoropopliteal Chroni Total Occlusions" Journal of Vascular Surgery, vol. 53, No. 5, pp. 1260-1264, May 2011.
EP Application No. 14180760.2, Extended European Search Report, mailed Jan. 29, 2015.

* cited by examiner

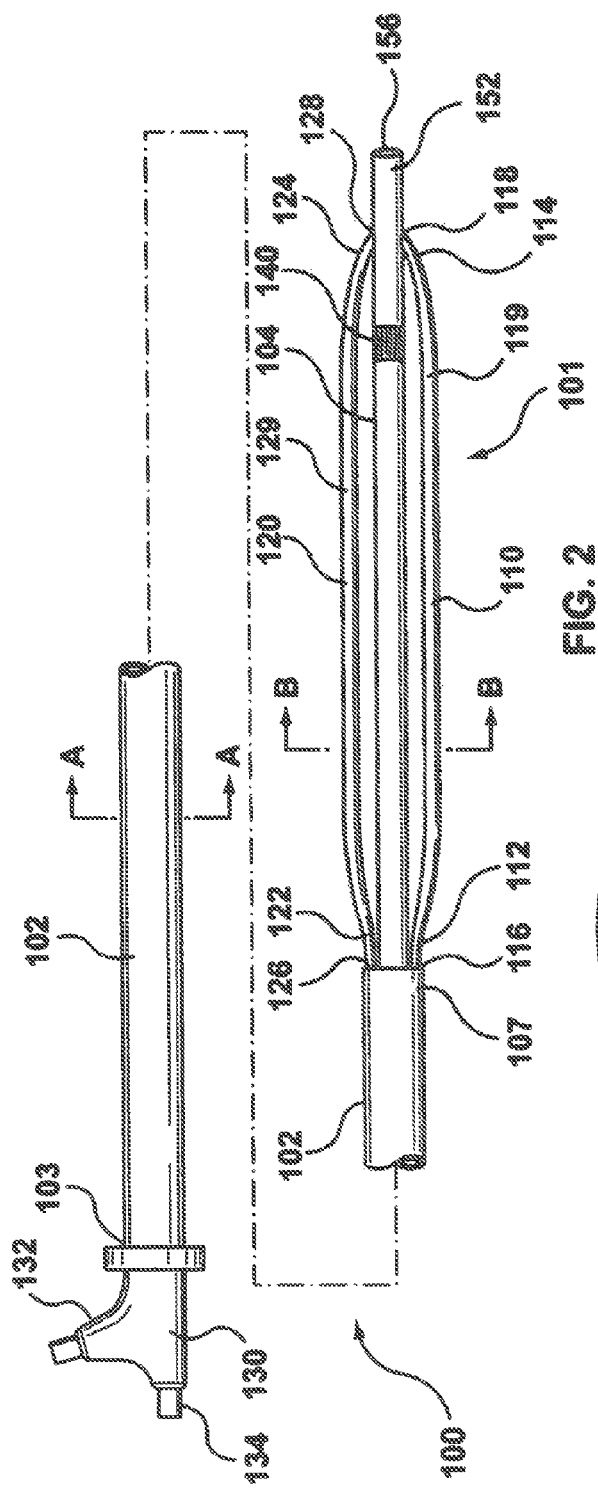
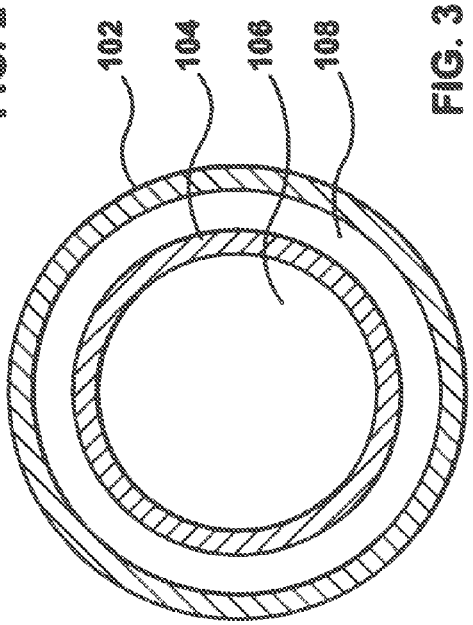

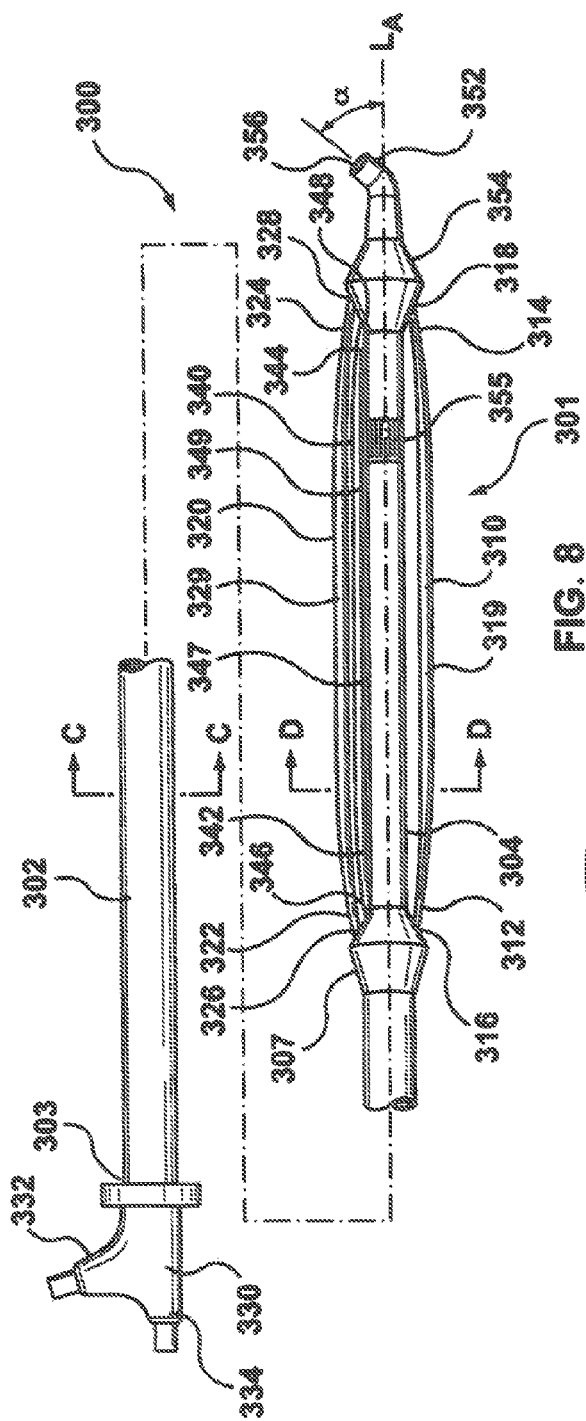
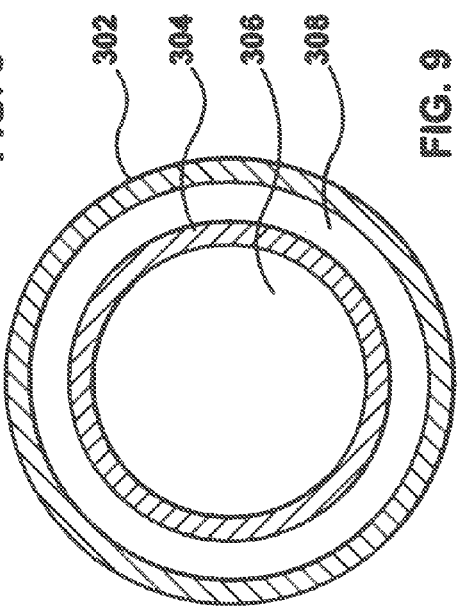

BALLOON CATHETER SYSTEMS AND METHODS FOR BYPASSING AN OCCLUSION IN A BLOOD VESSEL

FIELD OF THE INVENTION

The invention relates generally to a catheter system and a method of using the catheter system in combination with a guidewire for subintimally bypassing a blockage in a blood vessel such as a chronic total occlusion and reentering the true lumen of the blood vessel beyond the blockage.

BACKGROUND OF THE INVENTION

Cardiovascular disease, including atherosclerosis, is the leading cause of death in the United States. One method for treating atherosclerosis and other forms of arterial lumen narrowing is percutaneous transluminal angioplasty, commonly referred to as "angioplasty" or "PTA," or "PTCA" when performed in the coronary arteries. The objective in angioplasty is to restore adequate blood flow through the affected artery, which may be accomplished by inflating a balloon of a balloon catheter within the narrowed lumen of the artery to dilate the vessel.

The anatomy of arteries varies widely from patient to patient. Often, patient's arteries are irregularly shaped, highly tortuous and very narrow. The tortuous configuration of the arteries may present difficulties to a clinician in advancement of the balloon catheter to a treatment site. In addition, in some instances, the extent to which the lumen is narrowed at the treatment site is so severe that the lumen is completely or nearly completely obstructed, which may be described as a total occlusion. Total or near-total occlusions in arteries can prevent all or nearly all of the blood flow through the affected arteries. If the occlusion has been established for a long period of time, the lesion may be referred to as a chronic total occlusion or CTO. Chronic total occlusions can occur in coronary as well as peripheral arteries. Chronic total occlusions are often characterized by extensive plaque formation and typically include a fibrous cap surrounding softer plaque material. This fibrous cap may present a surface that is difficult to penetrate with a conventional medical guidewire.

A number of devices have been developed and/or used for the percutaneous interventional treatment of CTOs, such as stiffer guidewires, low-profile balloons, laser light emitting wires, atherectomy devices, drills, drug eluting stents, and re-entry catheters. The factor that is most determinative of whether the interventionalist can successfully recanalize a CTO is the interventionalist's ability to advance a suitable guidewire from a position within the true lumen of the artery proximal to the CTO lesion, across the CTO lesion, i.e., either through the lesion or around it, and then back into the true lumen of the artery at a location distal to the CTO lesion.

The most common site of a peripheral arterial CTO is the superficial femoral artery (SFA). Lesions in this area tend to be long (20-30 cm) and involve bulky, calcified plaque which also includes atheroma and organized thrombus. Dr. Bolia developed a revasculaturization procedure as described in *Recanalisation of femoro-popliteal occlusions: Improving success rate by subintimal recanalisation*, Clinic Radiol, 40:325, 1989, by exploiting the subintimal space where a guidewire enters the subintimal space between the intima and adventitia layers, is subsequently advanced to a point distal to the occlusion, and then maneuvered to re-enter or puncture the vessel layers to enter the true lumen of the vessel. Once the guide wire has traversed through the subintimal layer and re-enters the true lumen of the vessel at a point distal to the occlusion, percutaneous balloon angioplasty is performed to restore blood flow through subintimal recanalization.

Different devices have been developed for facilitating re-entry into the true lumen when using the subintimal approach of bypassing a CTO, such as the PIONEER® catheter system by Medtronic, Inc. Some of these re-entry devices may be complex and costly. Accordingly, there is a need for an effective and cost-effective catheter for use with a guidewire to subintimally bypass a CTO.

BRIEF SUMMARY OF THE INVENTION

Embodiments hereof are directed to catheter used in conjunction with a subintimal reentry guidewire. The catheter includes a catheter shaft, a first balloon, and a second balloon. The catheter shaft has a shaft longitudinal axis and a guidewire lumen disposed therethrough. The first balloon is coupled to an exterior of the catheter shaft at a proximal portion and a distal portion of the first balloon, with the portion of the first balloon between the proximal and distal portions not coupled to the catheter shaft. Similarly, second balloon is coupled to an exterior of the catheter shaft at a proximal portion and a distal portion of the second balloon, with the portion of the second balloon between the proximal and distal portions not coupled to the catheter shaft. The catheter shaft is external to both the first balloon and the second balloon and is disposed between the first and second balloons. When the balloons are uninflated and not subject to exterior forces, the longitudinal axes of the first balloon, second balloon, and catheter shaft lie in a common plane. When the catheter is disposed in the subintima of a vessel and the first balloon and the second balloon are inflated, the catheter shaft bends such that a tip of the catheter shaft distal of the first and second balloons is oriented towards a true lumen of the vessel.

Embodiments hereof are also directed to methods of bypassing an occlusion in a vessel. The method includes advancing a catheter in the true lumen of the vessel proximal to the occlusion, into a subintimal space between layers of the vessel wall proximal to the occlusion, and within the subintimal space such that a distal end of the catheter is distal of the occlusion. The method further includes inflating first and second balloons of the catheter such that a catheter shaft of the catheter is bent and the distal tip of the catheter shaft is directed towards the true lumen distal of the occlusion.

Embodiments hereof are also directed to catheter used in conjunction with a subintimal reentry guidewire. The catheter includes a catheter shaft including a guidewire lumen disposed therethrough, a first balloon, a second balloon, and a third balloon. The first balloon and second balloon are coupled to an exterior of the catheter shaft at a proximal portion and a distal portion thereof, respectively, with the first and second balloons not coupled to the catheter shaft between the proximal and distal connections. The catheter shaft is disposed exterior to and between the first and second balloons. A third balloon is coupled to an exterior of the catheter shaft ad is disposed between the catheter shaft and the second balloon. The third balloon is coupled to the catheter shaft along the length of the balloon. When the balloons are uninflated and not subject to exterior forces, the longitudinal axes of the first balloon, second balloon, third balloon, and catheter shaft lie in a common plane. When the catheter is disposed in the subintima of a vessel and the first balloon, second, and third balloons are inflated, the third balloon and catheter shaft rotate relative to the first and second balloons such that a distal tip of the catheter also rotates and is oriented towards a true lumen of the vessel distal of the occlusion.

Embodiments hereof are also directed to methods of bypassing an occlusion in a vessel. The method includes advancing a catheter in the true lumen of the vessel proximal to the occlusion, into a subintimal space between layers of the vessel wall proximal to the occlusion, and within the subintimal space such that a distal end of the catheter is distal of the occlusion. The method further includes inflating first, second, and third balloons of the catheter such that a catheter shaft of the catheter is rotated to orient a distal tip of the catheter shaft towards the true lumen distal of the occlusion.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 2 is a schematic illustration of a catheter system for use with a reentry guidewire according to an embodiment hereof.

FIG. 3 is a sectional view taken along line A-A of FIG. 2.

FIG. 8 is a schematic illustration of a catheter system for use with a reentry guidewire according to an embodiment hereof.

FIG. 9 is a sectional view taken along line C-C of FIG. 2.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" and "distally" are positions distant from or in a direction away from the clinician. "Proximal" and "proximally" are positions near or in a direction toward the clinician.

The following detailed description is merely exemplary in nature and is not intended to limit the invention or the application and uses of the invention. Although the description of the invention is in the context of treatment of blood vessels such as smaller diameter peripheral or coronary arteries, the invention may also be used in any other body passageways where it is deemed useful. Although the description of the invention generally refers to a system and method of bypassing a vessel blockage in a proximal-to-distal direction, i.e. antegrade or with the blood flow, the invention may be used equally well to bypass a vessel blockage in a distal-to-proximal direction, i.e. retrograde or against the blood flow if access is available from that direction. In other terms, the system and method described herein may be considered to bypass a vessel blockage from a near side of the blockage to a far side of the blockage. Furthermore, there is no intention to be bound by any expressed or implied theory presented in the preceding technical field, background, brief summary or the following detailed description.

Figure 1:
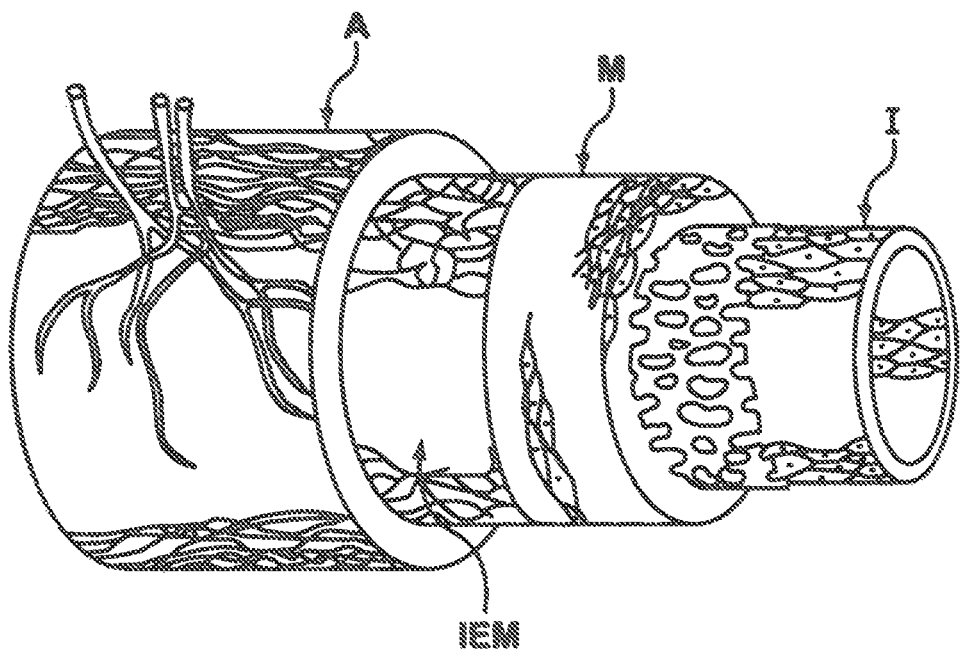
FIG. 1 is a diagram of an artery showing the three layers of tissue that comprise the artery wall.

FIG. 1 is a sectional view of the anatomy of an artery wall, which for purposes of this description is shown to consist essentially of three layers, the tunica intima I ("intima"), tunica media M ("media") which is the thickest layer of the wall, and the tunica adventitia A ("adventitia"). In some arteries an internal elastic membrane IEM is disposed between the media M and adventitia A. The adventitia A is made of collagen, vasa vasorum and nerve cells, the media M is made of smooth muscle cells, and the intima I is made up of a single layer of endothelial cells that provide a nonthrombogenic surface for flowing blood.

Embodiments hereof relate to a system and method for re-entering the true lumen of a vessel after subintimally bypassing an occlusion in a blood vessel such as a chronic total occlusion (CTO) of an artery. With references to FIGS. 2-4, a catheter 100 according to an embodiment hereof includes a main or outer shaft 102 having a proximal end 103 and a distal end 107. Coupled to proximal end 103 of shaft 102 is a handle or luer 130, as will be described in more detail below.

More particularly, with reference FIGS. 2-3, the proximal portion of catheter 100 includes outer shaft 102 and an inner shaft 104 disposed within outer shaft 102. Inner shaft defines a guidewire lumen 106. An inflation lumen 108 is defined between an outer surface of inner shaft 104 and an inner surface of outer shaft 102, as shown in FIG. 3. Guidewire lumen 106 may have a diameter to receive therein a guidewire with a diameter in the range of 0.014 inch to 0.035 inch. However, those skilled in the art would recognize that the size of guidewire lumen 106 may be different if catheter 100 is configured to be used with a different size guidewire. Inflation lumen 108 is sized such that an inflation fluid may pass therethrough to inflate balloons disposed at the distal portion of catheter 100, as described in more detail herein. In a non-limiting embodiment, guidewire lumen 104 has a diameter of 0.035 inch, inner shaft 104 has a wall thickness of 0.10 mm, and outer shaft 102, has an outer diameter of 1.45 mm and a wall thickness of 0.10 mm. As would be understood by those skilled in the art, other sizes may be utilized for outer shaft 102 and inner shaft 104. Further, although a co-axial construction is shown in FIG. 3, other types of catheter constructions may be used, such as, without limitation thereto, a catheter shaft formed by multi-lumen profile extrusion that includes a guidewire lumen and an inflation lumen. In another embodiment hereof (not shown), catheter 100 may be modified to be of a rapid exchange (RX) catheter configuration without departing from the scope of the present invention such that guidewire shaft 104 extends within only the distal portion of outer shaft 102, as known to those skilled in the art.

A distal portion 101 of catheter 100 includes inner shaft 104, a first balloon 110, and a second balloon 120. Inner shaft 104 extends distally beyond distal end 107 of outer shaft 102, as shown in FIG. 2. Although inner shaft 104 is shown as a continuous shaft, those skilled in the art would recognize that inner shaft 104 may comprise different portions of shaft attached to each other. In particular, the portion of inner shaft 104 extending distally beyond distal end 107 of outer shaft 102 may be of a different construction than a proximal portion of inner shaft 104. In one exemplary embodiment, the distal portion of inner shaft 104 is more flexible than the proximal portion of inner shaft 104.

A proximal end or neck 112 of first balloon 110 is coupled to distal end 107 of outer shaft 102 at a proximal connection or bond 116. Similarly, a distal end or neck 114 of first balloon 110 is coupled to a distal portion of inner shaft 104 at a distal connection or bond 118. An outer surface of inner shaft 104 between the proximal and distal bonds 116, 118 is not bonded or otherwise coupled to first balloon 110. Inflation lumen 108 is in fluid communication with the interior 119 of first balloon 110. The distance or length between proximal bond 116 and distal bond 118, in which first balloon 110 and inner shaft 104 are not coupled together, is equal to or slightly less than the length of first balloon 110 prior to inflation thereof. Proximal and distal bonds 116, 118 may be formed in any conventional manner known to one of skill in the art of balloon catheter construction, such as by laser welding, adhesives, heat fusing, or ultrasonic welding.

Similarly, a proximal end or neck 122 of second balloon 120 is coupled to distal end 107 of outer shaft 102 at a proximal connection or bond 126. A distal end or neck 124 of second balloon 120 is coupled to the distal portion of inner shaft 104 at a distal connection or bond 128. An outer surface of inner shaft 104 between the proximal and distal bonds 126, 128 is not bonded or otherwise coupled to second balloon 120. Inflation lumen 108 is in fluid communication with the interior 129 of second balloon 120. The distance or length between proximal bond 126 and distal bond 128, in which second balloon 120 and inner shaft 104 are not coupled together, is equal to or slightly less than the length of second balloon 120 prior to inflation thereof. Proximal and distal bonds 126, 128 may be formed in any conventional manner known to one of skill in the art of balloon catheter construction, such as by laser welding, adhesives, heat fusing, or ultrasonic welding.

Figure 4:
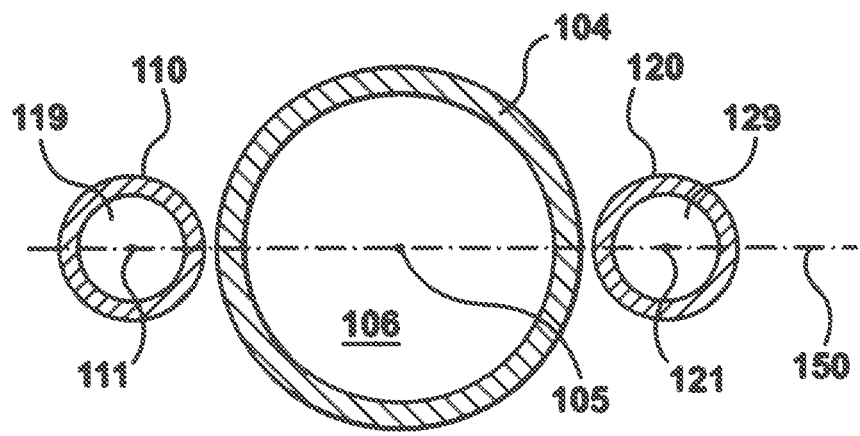
FIG. 4 is a sectional view taken along line B-B of FIG. 2.

As can be seen in FIGS. 2 and 4, first and second balloons 110, 120 are coupled to inner shaft 104 such that first and second balloons 110, 120 are disposed outside of inner shaft 104 and inner shaft 104 is disposed outside of first and second balloons 110, 120. Further, as shown in FIG. 4, when uninflated and without outside forces acting on the first and second balloons 110, 120, a longitudinal axis 111 of first balloon 110, a longitudinal axis 121 of second balloon 120, and a longitudinal axis 105 of inner shaft 104 lie generally in a common plane 150. Further, although described as uninflated, the longitudinal axes 111, 121, and 105 lie generally in a common plane when first and second balloons are inflated, but without outside forces acting on first and second balloons 110, 120. When the catheter 100 is introduced into the subintimal space, the co-planarity of axes 111, 121 and 105 is no longer guaranteed because of the vessel curvature. In fact, due to the vessel curvature, the inner shaft 104 will assume a different position with respect to first and second balloons 110, 120. This configuration will be even more evident when first and second balloons 110, 120 are inflated. By the term "generally in a common plane", it is meant that the axes 111, 121, 105 need not lie perfectly along a common plane, but within 5 degrees of a common plane.

Inner shaft 104 and outer shaft 102 extend out proximally a sufficient length to extend out of the patient and are coupled to a hub 130. Coupled to a proximal portion of proximal portion 102 is a handle or hub 130, such as a Tuohy-Burst luer. In the embodiment shown, hub 130 includes a first arm or branch 132 and a second arm or branch 134. First branch 132 includes a first proximal opening leading to a first lumen. The first lumen is in fluid communication with inflation lumen 108. Second branch 134 includes a second proximal opening and a second lumen in communication with guidewire lumen 106. Hub 130 may be overmolded or otherwise coupled to proximal portion 103 of outer shaft 102. Hub 130 may also include other features known to those skilled in the art, such as a strain relief member, hemostatic valves, etc.

A radiopaque marker 140 may be disposed on inner shaft 104 to be imageable by an imaging apparatus for aiding a clinician in identifying that catheter 100 is in the correct position at the treatment site, as explained in more detail below. Optionally, catheter 100 may incorporate additional radiopaque markers (not shown) strategically located along the length of catheter 100 to for aiding a clinician in delivery of catheter 100 to a correct position at the treatment site.

Figure 5:
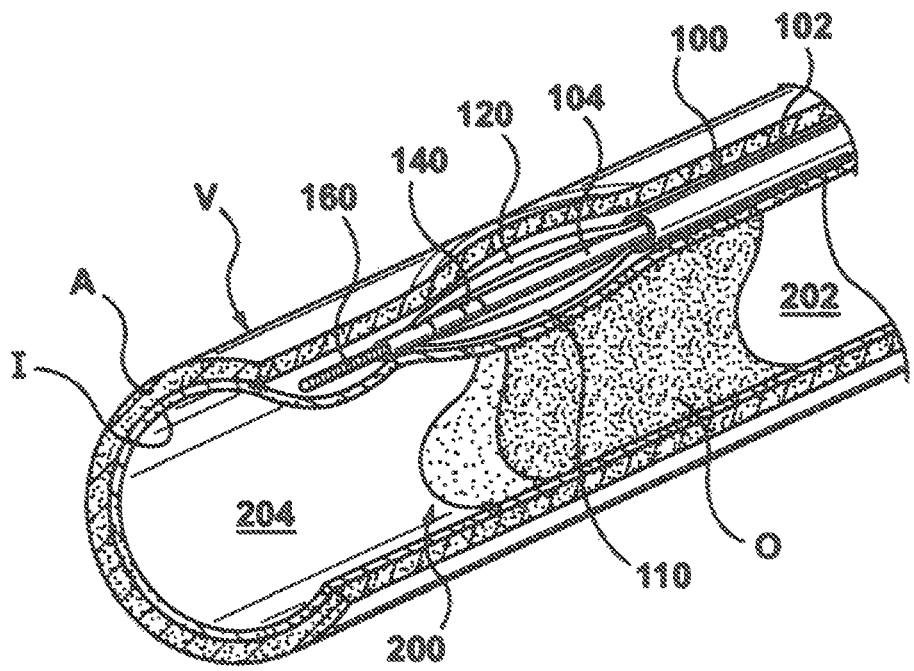
FIGS. 5-7 illustrate steps of utilizing the catheter system of FIG. 2 with a subintimal reentry guidewire to bypass a chronic total occlusion according to an embodiment hereof.
Figure 6:
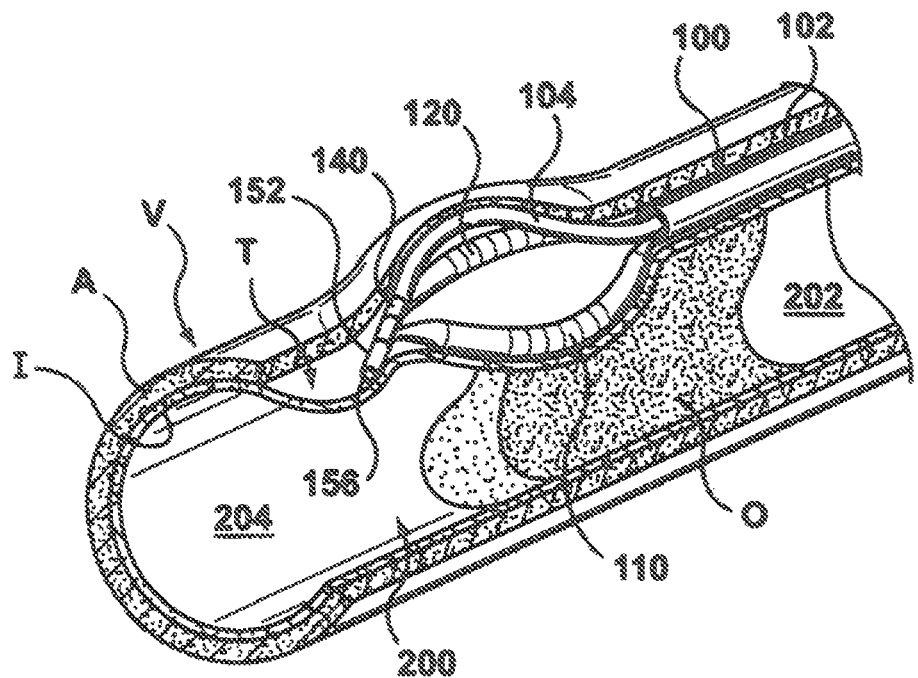
Figure 7:
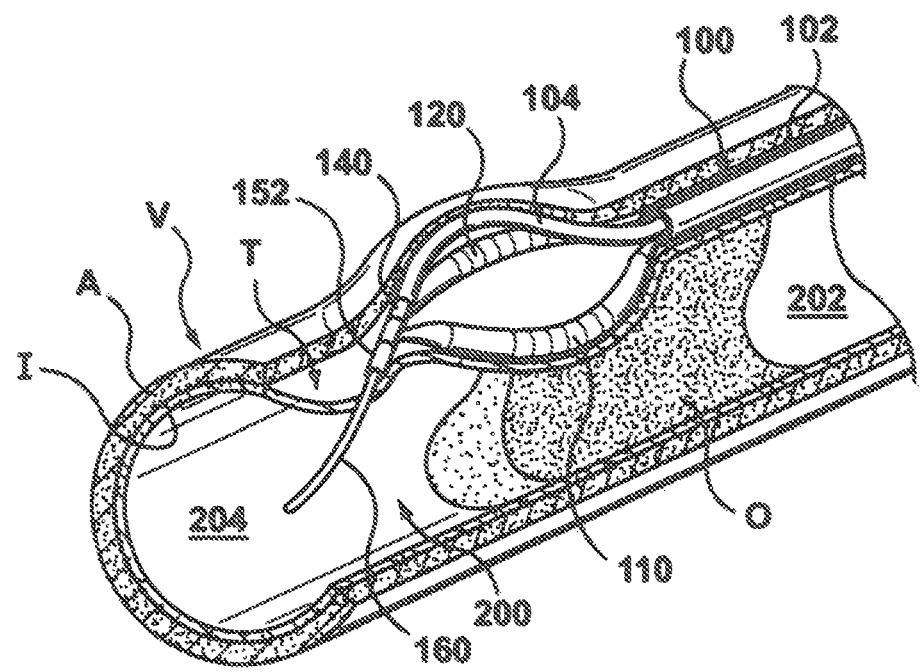

FIGS. 5-7 illustrate a prophetic method of using the above-described catheter 100 to support a subintimal reentry guidewire 160 to bypass a chronic total occlusion O according to an embodiment hereof. Subintimal reentry guidewire 160 can be any subintimal reentry guidewire known to those skilled in the art, or future subintimal reentry guidewires developed, as the present invention is directed to catheter 100 and its use with the subintimal reentry guidewire. FIGS. 5-7 illustrate only the intima I and adventia A layers of the vessel V for convenience of the illustration. Accordingly, as shown in FIGS. 5-7 and described in more detail below, catheter 100 and subintimal reentry guidewire 160 are advanced between the intima I and the media M layers of the vessel V. Catheter 100 and subintimal reentry guidewire 160 may be used as part of a system for creating a subintimal reentry conduit within a wall of a blood vessel V, such as an artery located below the knee of a patient, to allow blood flow around the occlusion. Although described in relation to bypassing a chronic total occlusion O, it should be understood that the methods and apparatus described herein may be used for bypassing any tight stenoses in arteries or other anatomical conduits and are not limited to total occlusions. Typically, a guiding catheter and/or an introducer sheath (not shown) are first inserted percutaneously into a femoral artery of a patient. Subintimal reentry guidewire 160 is inserted into a guiding catheter and maneuvered through the vasculature to a treatment site, which in this instance is shown as a total occlusion O within a lumen 200 of blood vessel V.

In accordance with techniques known in the field of interventional cardiology and/or interventional radiology, subintimal reentry guidewire 160 is transluminally advanced through lumen 200 of blood vessel V to a position upstream 202 of occlusion O. Subintimal reentry guidewire 160 pierces the intima I and is advanced distally to create a subintimal tract T by locally dissecting or delaminating intima I from media M. In order to pierce the intima I, a clinician may manipulate the distal end of the subintimal reentry guidewire 160 by prolapsing or bending-over the distal end of subintimal reentry guidewire 160 and thereafter may use the stiffer arc of the prolapsed distal end to pierce into the intima I to advance subintimal reentry guidewire 160 there through. The piercing of the intima I is aided by the fact that typically blood vessel V is diseased, which in some instances makes the intima I prone to piercing. Subintimal reentry guidewire 160 is transluminally advanced within the subintimal tract T from a proximal side of occlusion O distally.

With the tip of guidewire 160 located distally of occlusion O, which may be confirmed by imaging, guidewire 160 is backloaded into catheter 100 by inserting a proximal end (not shown) of guidewire 160 into a distal opening 156 of catheter 100, as known in the art. Catheter 100 is advanced distally over guidewire 160 through lumen 200 and into subintimal tract T, resulting in catheter 100 disposed through in the position shown in FIG. 5. A clinician may confirm that catheter 100 is in the position shown in FIG. 5 by identifying radiopaque marker 140 using an imaging apparatus, as known to those skilled in the art.

With catheter 100 in the location shown in FIG. 5, guidewire 160 is drawn back into catheter 100. First and second balloons 110, 120 are then simultaneously inflated, as shown in FIG. 6, by injecting an inflation fluid into the first lumen of first branch 132 of hub 130 described above. The inflation fluid advances through the first lumen into inflation lumen 108 and into interiors 119, 129 of first and second balloon 110, 120, respectively. Inflation of first and second balloons 110, 120 results in stabilizing catheter 100 in the subintimal space because first and second balloons 110, 120, in the inflated configuration, lay between and against the layers of the vessel wall, such as first balloon laying against the intima and second balloon 120 laying against the adventitia A, as shown in FIG. 6. Further, as shown in FIGS. 5-7, the blood vessel V is curved, that it, it is in the general form of a tube such that the wall of the blood vessel is curved. Accordingly, because catheter 100 follows the curvature of the vessel wall and the configuration of first and second balloons 110, 120 with respect to inner shaft 104, when first and second balloons 110, 120 are inflated, the distal portion of inner shaft 104 is compressed in the region between first and second balloons 110, 120 and caused to assume the curved configuration shown in FIGS. 6 and 7, such that the catheter distal tip 152 is oriented in the direction of the true lumen. An outer diameter of each of first and second balloons 110, 120 after inflation is in the range of 1-3 millimeters. However, those skilled in the art would recognize that any suitable diameter suitable for a particular application may be utilized.

After first and second balloon 110, 120 are inflated and distal tip 152 is oriented towards the true lumen 204 distal of the occlusion O, guide wire 160 is re-advanced distally out of distal opening 156 of inner shaft 104 to perforate the intima I distal of occlusion and enter true lumen 204 distal of occlusion O, as shown in FIG. 7. Guide wire 160 may be the same guidewire used to guide catheter 100 into the subintimal tract T or may be a different guidewire. For example, and not by way of limitation, guidewire 160 may be removed and a second guidewire with a stiffer tip or other desirable feature for penetrating the intima I may be loaded into guidewire lumen 106 of catheter 100 and extended distally from distal opening 156. In another embodiment, guidewire 160 may be removed and another suitable tool, such as but not limited to a microcatheter or a needle or a stylet, may be loaded into guidewire lumen 106 and extended out of distal opening 156 to perforate the intima I and access true lumen 204 distal of occlusion O.

Figure 16:
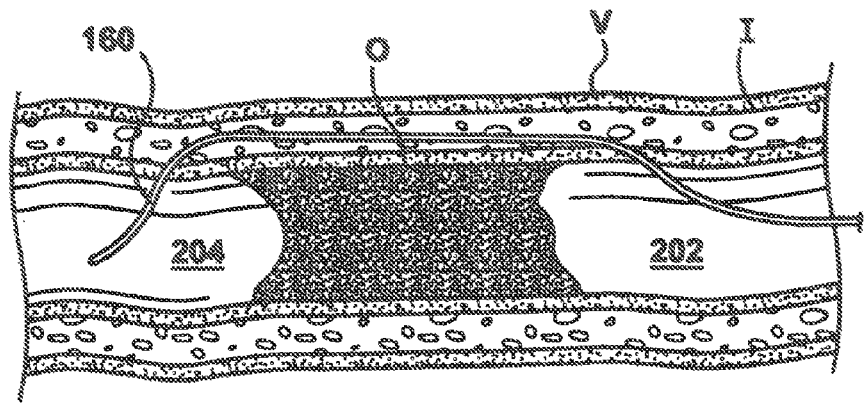
FIG. 16-18 illustrate steps of delivering a stent to a position where a distal end of the stent is in the true lumen downstream of the occlusion, a proximal end of the stent is in the true lumen upstream of the occlusion, and a mid-portion of the stent extends through the subintimal conduit.

With guidewire 160 extending from outside of the patient into true lumen 202 proximal of occlusion O, into and within subintimal tract T, and out of subintimal tract T into true lumen 204 distal of occlusion O, first and second balloons 110, 120 are deflated and catheter 100 may then be removed. Further steps for delivering a stent may be performed as described below with respect to FIGS. 16-18.

According to another embodiment hereof shown in FIG. 8-15, a catheter 300 includes a main or outer shaft 302 having a proximal end 303 and a distal end 307. Coupled to proximal end 303 of outer shaft 302 is a handle or luer 330, as will be described in more detail below.

Figure 10:
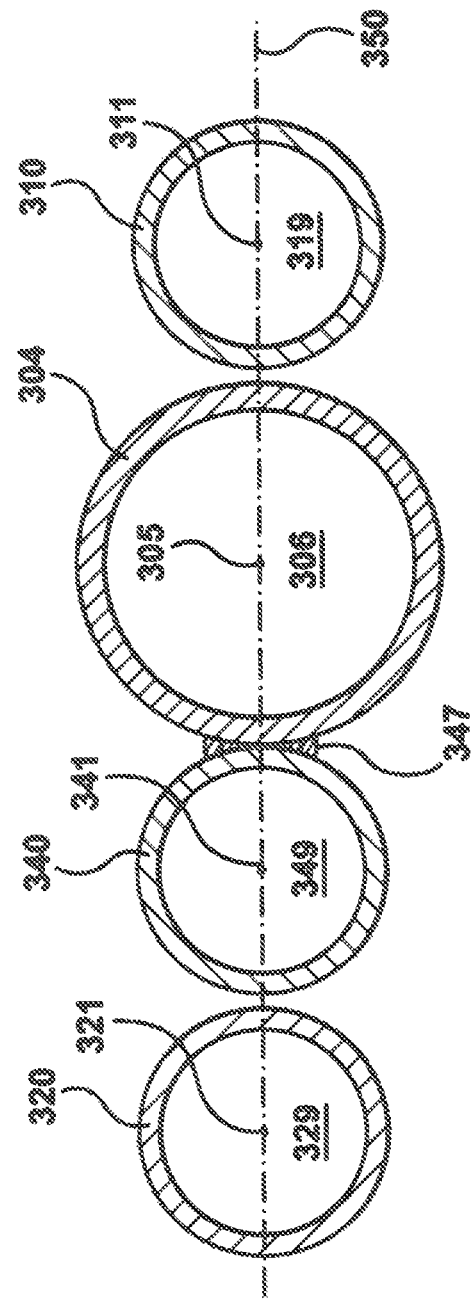
FIG. 10 is a sectional view taken along line D-D of FIG. 8.

More particularly, with reference FIGS. 8-10, the proximal portion of catheter 300 includes outer shaft 302 and an inner shaft 304 disposed within outer shaft 302. Inner shaft defines a guidewire lumen 306. An inflation lumen 308 is defined between an outer surface of inner shaft 304 and an inner surface of outer shaft 302, as shown in FIG. 9. Guidewire lumen 306 may have a diameter to receive therein a guidewire with a diameter in the range of 0.014 inch to 0.035 inch. However, those skilled in the art would recognize that the size of guidewire lumen 306 may be different if catheter 300 is configured to be used with a different size guidewire. Inflation lumen 308 is sized such that an inflation fluid may pass therethrough to inflate balloons disposed at the distal portion of catheter 300, as described in more detail herein. In a non-limiting embodiment, guidewire lumen 304 has a diameter of 0.035 inch, inner shaft 304 has a wall thickness of 0.10 mm, and outer shaft 302, has an outer diameter of 1.45 mm and a wall thickness of 0.10 mm. As would be understood by those skilled in the art, other sizes may be utilized for outer shaft 302 and inner shaft 304. Further, although a co-axial construction is shown in FIG. 9, other types of catheter constructions may be used, such as, without limitation thereto, a catheter shaft formed by multi-lumen profile extrusion that includes a guidewire lumen and an inflation lumen. In another embodiment hereof (not shown), catheter 300 may be modified to be of a rapid exchange (RX) catheter configuration without departing from the scope of the present invention such that guidewire shaft 304 extends within only the distal portion of outer shaft 302, as known to those skilled in the art.

A distal portion 301 of catheter 300 includes inner shaft 304, a first balloon 310, a second balloon 320, and a third balloon 340. Inner shaft 304 extends distally beyond distal end 307 of outer shaft 302, as shown in FIG. 8. Although inner shaft 304 is shown as a continuous shaft, those skilled in the art would recognize that inner shaft 304 may comprise different shafts attached to each other. In particular, the portion of inner shaft 304 extending distally beyond distal end 307 of outer shaft 302 may be of a different construction than a proximal portion of inner shaft 304. In one exemplary embodiment, the distal portion of inner shaft 304 is more flexible than the proximal portion of inner shaft 304.

A proximal end or neck 312 of first balloon 310 is coupled to distal end 307 of outer shaft 302 at a proximal connection or bond 316 such that inflation lumen 308 between outer shaft 302 and inner shaft 304 is in fluid communication with an interior 319 of first balloon 310. Similarly, a distal end or neck 314 of first balloon 310 is coupled to a distal portion 354 of inner shaft 304 at a distal connection or bond 318. An outer surface of inner shaft 304 between the proximal and distal bonds 316, 318 is not bonded or otherwise coupled to first balloon 310. The distance or length between proximal bond 316 and distal bond 318, in which first balloon 310 and inner shaft 304 are not coupled together, is equal to or slightly less than the length of first balloon 310 prior to inflation thereof. Proximal and distal bonds 316, 318 may be formed in any conventional manner known to one of skill in the art of balloon catheter construction, such as by laser welding, adhesives, heat fusing, or ultrasonic welding.

Similarly, a proximal end or neck 322 of second balloon 320 is coupled to distal end 307 of outer shaft 302 at a proximal connection or bond 326 such that inflation lumen 308 between outer shaft 302 and inner shaft 304 is in fluid communication with an interior 329 of second balloon 320. A distal end or neck 324 of second balloon 320 is coupled to distal portion 354 of inner shaft 304 at a distal connection or bond 328. An outer surface of inner shaft 304 between the proximal and distal bonds 326, 328 is not bonded or otherwise coupled to second balloon 320. Similarly, an outer surface of third balloon 340 disposed between second balloon 320 and inner shaft 304, described in more detail below, is not bonded or otherwise coupled to second balloon between proximal and distal bonds 326, 328. The distance or length between proximal bond 326 and distal bond 328, in which second balloon 320 and inner shaft 304 are not coupled together, is equal to or slightly less than the length of second balloon 320 prior to inflation thereof. Proximal and distal bonds 326, 328 may be formed in any conventional manner known to one of skill in the art of balloon catheter construction, such as by laser welding, adhesives, heat fusing, or ultrasonic welding.

Third balloon 340 is disposed between second balloon 320 and inner shaft 304, as shown in FIGS. 8 and 10. A proximal end or neck 342 of second balloon 320 is coupled to distal end 307 of outer shaft 302 at a proximal connection or bond 346 such that inflation lumen 308 between outer shaft 302 and inner shaft 304 is in fluid communication with an interior 349 of third balloon 340. A distal end or neck 344 of third balloon 340 is coupled to distal portion 354 of inner shaft 304 at a distal connection or bond 348. Further, an outer surface of inner shaft 304 between the proximal and distal bonds 346, 348 is bonded or coupled to third balloon 340 at longitudinal bond 347. As would be apparent to those skilled in the art, bonds, 346, 347, 348 may be a single, continuous bond between third balloon 340 and distal end 307/inner shaft 304. Further, proximal and distal bonds 346, 348 may be separate bonds from longitudinal bond 347. Further, although longitudinal bond 347 is described herein as a continuous bond, those skilled in the art would recognize that longitudinal bond may be a series of discrete, individual bonds that have the effect of a lengthwise or longitudinal bond. As noted above, an outer surface of third balloon 340, opposite longitudinal bond 347, faces an outer surface of second balloon 320 but is not coupled thereto. Bonds 346, 347, 348 may be formed in any conventional manner known to one of skill in the art of balloon catheter construction, such as by laser welding, adhesives, heat fusing, or ultrasonic welding.

As can be seen in FIGS. 8 and 10, first, second, and third balloons 310, 320, and 340 are coupled to inner shaft 304 such that first, second, and third balloons 310, 320, 340 are disposed outside of inner shaft 304 and inner shaft 304 is disposed outside of first, second, and third balloons 310, 320, 340. Further, as shown in FIG. 10, when uninflated and without outside forces acting thereon, a longitudinal axis 311 of first balloon 310, a longitudinal axis 321 of second balloon 120, a longitudinal axis 341 of third balloon 340, and a longitudinal axis 305 of inner shaft 304 lie generally in a common plane 350. By the term "generally in a common plane", it is meant that the axes 311, 321, 341, and 305 need not lie perfectly along a common plane, but within 5 degrees of a common plane.

Inner shaft 304 and outer shaft 302 extend out proximally a sufficient length to extend out of the patient and are coupled to a handle or hub 330, such as a Tuohy-Burst luer. In the embodiment shown, hub 330 includes a first arm or branch 332 and a second arm or branch 334. First branch 332 includes a first proximal opening leading to a first lumen. The first lumen is in fluid communication with inflation lumen 308. Second branch 334 includes a second proximal opening and a second lumen in communication with guidewire lumen 306. Hub 330 may be overmolded or otherwise coupled to proximal portion 303 of outer shaft 302. Hub 330 may also include other features known to those skilled in the art, such as a strain relief member, hemostatic valves, etc.

A radiopaque marker 355 may be disposed on inner shaft 304 to be imageable by an imaging apparatus for aiding a clinician in identifying that catheter 300 is in the correct position at the treatment site, as explained in more detail below. Optionally, catheter 300 may incorporate additional radiopaque markers (not shown) strategically located along the length of catheter 300 for aiding the clinician in delivery of catheter 300 to a correct position at the treatment site.

Catheter 300 also includes a distal tip 352 disposed distal of distal portion 354 of inner shaft 304. In the embodiment of FIGS. 8-15, distal tip 352 is angled at an angle $\alpha$ with respect to a longitudinal axis $L_A$ of catheter 300. Angle $\alpha$ may be in the range of 30° to 60°.

Figure 11:
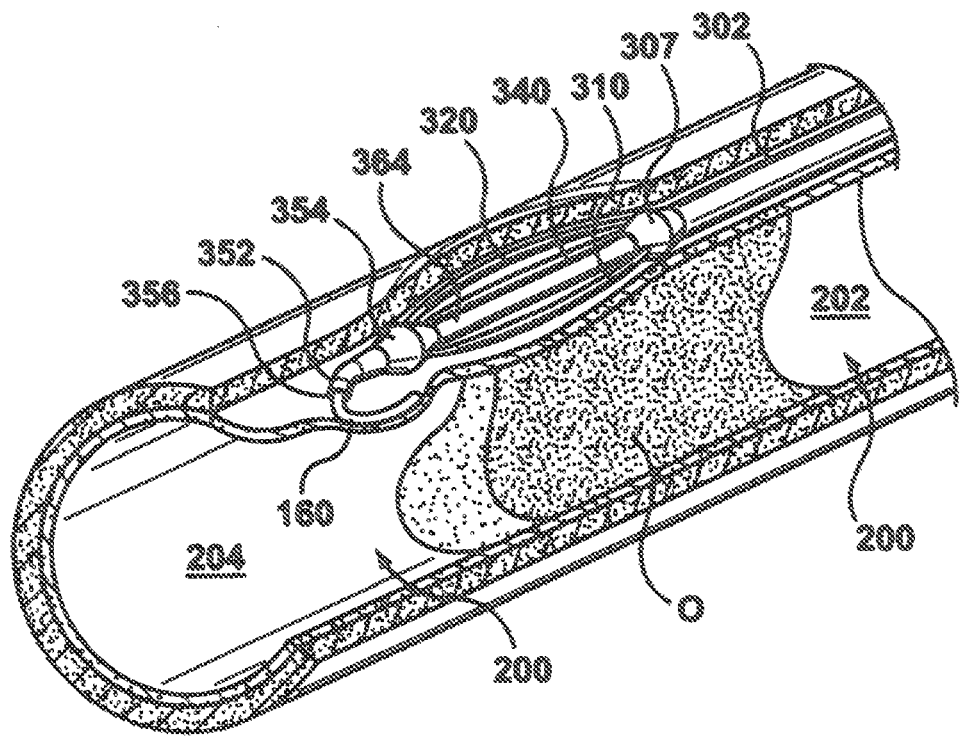
FIGS. 11-15 illustrate steps of utilizing the catheter system of FIG. 8 with a subintimal reentry guidewire to bypass a chronic total occlusion according to an embodiment hereof.
Figure 12:
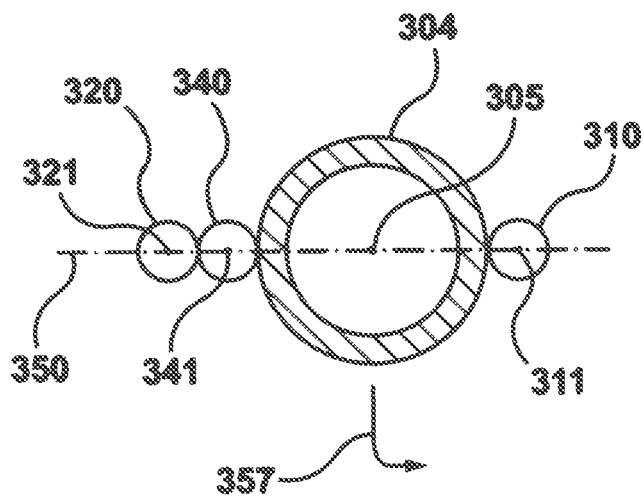
Figure 13:
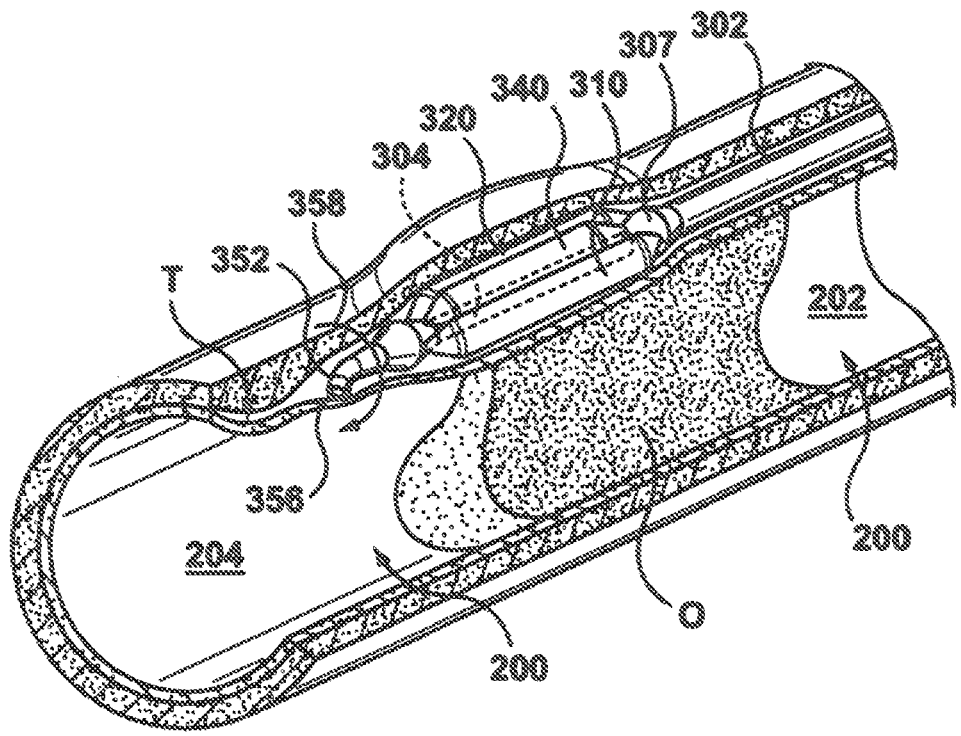
Figure 14:
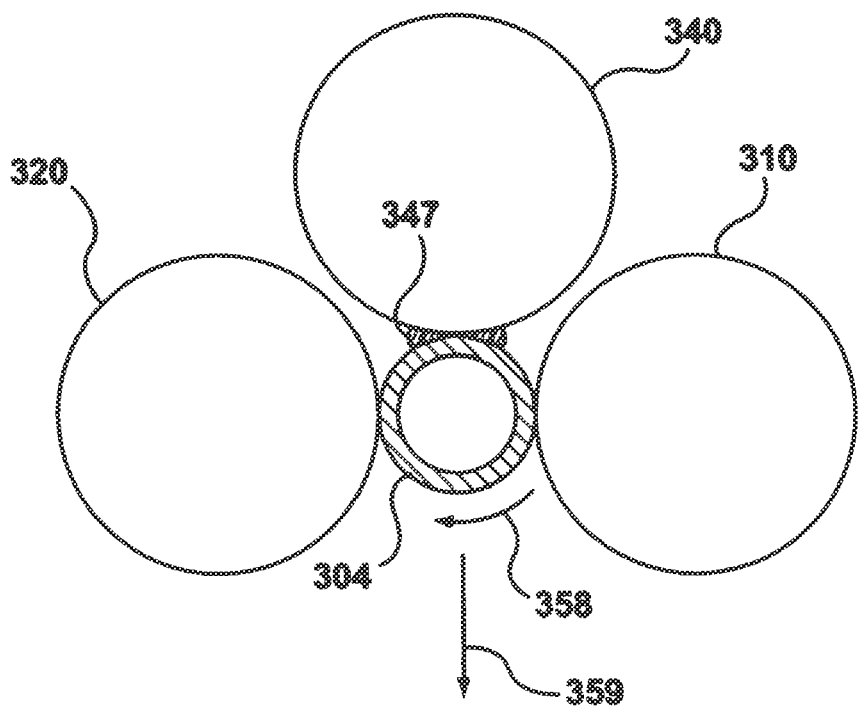
Figure 15:
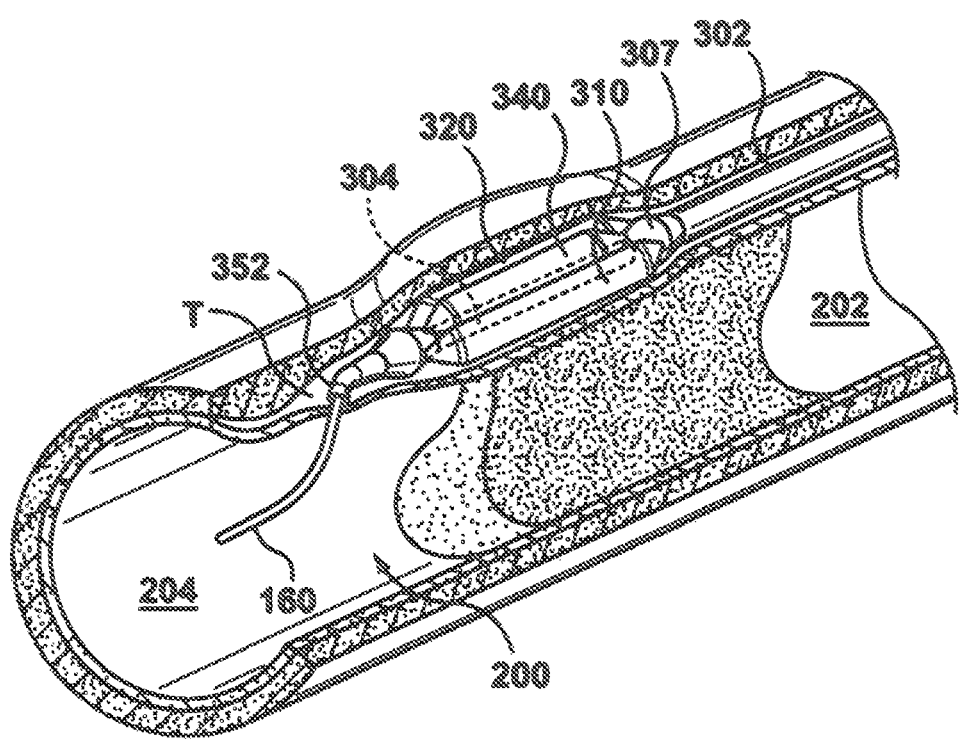

FIGS. 11-15 illustrate a prophetic method of using the above-described catheter 300 to support a subintimal reentry guidewire 160 to bypass a chronic total occlusion O according to an embodiment hereof. Subintimal reentry guidewire 160 can be any subintimal reentry guidewire known to those skilled in the art, or future subintimal reentry guidewires developed, as the present invention is directed to catheter 300 and its use with the subintimal reentry guidewire. FIGS. 11, 13, and 15 illustrate only the intima I and adventia A layers of the vessel V for convenience of the illustration. Accordingly, as shown in FIGS. 11-15 and described in more detail below, catheter 300 and subintimal reentry guidewire 160 are advanced between the intima I and media M layers of the vessel V. Catheter 300 and subintimal reentry guidewire 160 may be used as part of a system for creating a subintimal reentry conduit within a wall of a blood vessel V, such as an artery located below the knee of a patient, to allow blood flow around the occlusion. Although described in relation to bypassing a chronic total occlusion O, it should be understood that the methods and apparatus described herein may be used for bypassing any tight stenoses in arteries or other anatomical conduits and are not limited to total occlusions. Typically, a guiding catheter and/or an introducer sheath (not shown) are first inserted percutaneously into a femoral artery of a patient. Subintimal reentry guidewire 160 is inserted into a guiding catheter and maneuvered through the vasculature to a treatment site, which in this instance is shown as a total occlusion O within a lumen 200 of blood vessel V.

In accordance with techniques known in the field of interventional cardiology and/or interventional radiology, subintimal reentry guidewire 160 is transluminally advanced through true lumen 200 of blood vessel V to a position upstream or proximal 202 of occlusion O. Subintimal reentry guidewire 160 pierces the intima I and is advanced distally to create a subintimal tract T by locally dissecting or delaminating intima I from media M. In order to pierce the intima I, a clinician may manipulate the distal end of the subintimal reentry guidewire 160 by prolapsing or bending-over the distal end of subintimal reentry guidewire 160 and thereafter may use the stiffer arc of the prolapsed distal end to pierce into the intima I to advance subintimal reentry guidewire 160 there through. The piercing of the intima I is aided by the fact that typically blood vessel V is diseased, which in some instances makes the intima I prone to piercing. Subintimal reentry guidewire 160 is transluminally advanced within the subintimal tract T from a proximal side of occlusion O distally.

With the tip of guidewire 160 located distally of occlusion O, which may be confirmed by imaging, guidewire 160 is backloaded into catheter 300 by inserting a proximal end (not shown) of guidewire 160 into distal opening 356 of catheter 300, as known in the art. Catheter 300 is advanced distally over guidewire 160 through lumen 200 and into subintimal tract T, resulting in catheter 300 disposed through in the position shown in FIG. 11. A clinician may confirm that catheter 300 is in the position shown in FIG. 11 by identifying radiopaque marker 355 using an imaging apparatus, as known to those skilled in the art.

With catheter 300 in the location shown in FIG. 11, inner shaft 304, first balloon 310, second balloon 320, and third balloon 340 are disposed along common plane 350, as shown in FIG. 12. Further, angled tip 352 is oriented as represented by arrow 357 in FIG. 12. As shown in FIG. 12, angled tip 352 is angled such that distal opening 356 is generally parallel to common plane 350. Although FIG. 12 shows arrow 357 below plane 350, this orientation is used to indicate that tip 352 is distal of balloons 310, 320, 340. As can be seen by the arrowhead in FIG. 12, angled distal tip 352 is directed generally in the direction of first balloon 310 relative to longitudinal axis 305 of inner shaft 304.

With catheter 300 in the location shown in FIG. 11, guidewire 160 is drawn back into catheter 300. First, second, and third balloons 310, 320, and 340 are then simultaneously inflated, as shown in FIG. 13, by injecting an inflation fluid into the first lumen of first branch 332 of hub 330 described above. Alternatively, inflation of the three balloons is not performed simultaneously. The inflation fluid advances through the first lumen into inflation lumen 308 and into interiors 319, 329, and 349 of first, second, and third balloons 310, 320, and 340, respectively. First, second, and third balloons 310, 320, and 340 are inflated to an outer diameter in the range of 1 to 3 millimeters. However, those skilled in the art would recognize that other diameter balloons may be utilized depending on the application. Inflation of first, second, and third balloons 310, 320, and 340 results in stabilizing catheter 100 in the subintimal space because first, second, and third balloons 310, 320, and 340 in the inflated configuration, lay between and against the layers of the vessel wall. Further, inflation of first, second, and third balloons 310, 320, 340 causes third balloon 340 to move between first and second balloons 310, 320. Because third balloon 340 is constrained by longitudinal bond 347 to inner shaft 304, when third balloon 340 moves between first and second balloons 310, 320, inner shaft 304 is rotated approximately 90 degrees with third balloon 340, as shown by arrow 358 in FIGS. 13 and 14. Tip 352 rotates with inner shaft 304 such that tip 352 is oriented in the direction of the lumen 200 distal of the occlusion O, as shown in FIG. 13 and represented by arrow 359 in FIG. 14. In an embodiment, third balloon 340 is approximately the same diameter as first balloon 310 and second balloon 320 such that, after being inflated, third balloon 340 touches first and second balloons 310, 320 and is supported by them, thereby favoring the 90° rotation of inner shaft 104.

As noted above, when catheter 300 is in the desired location shown in FIG. 11, catheter 300 lies on and follows the curvilinear profile of the vessel wall. Thus, when located within the subintimal tract, the longitudinal axes 311, 321, 341, and 305 are no longer located in a common plane. In particular, the curvature of the vessel wall causes longitudinal axes 311, 321 of first and second balloons 310, 320 to be displaced from longitudinal axes 341, 305 of third balloon 340 and inner shaft 304. This displacement is more stressed when balloons 310, 320, 340 are simultaneously inflated and the inflation of first and second balloons 310, 320, which are coupled to inner shaft only at their respective proximal necks 312, 322 and distal necks 314, 324, causes third balloon 340, which is coupled to inner shaft 304 along the length thereof, to be even more displaced from the common plane and thus to rotate the inner shaft 304 and thus its angled tip 352 therewith.

After first and second balloon 310, 320 are inflated and angled distal tip 352 is oriented towards the true lumen 204 distal of the occlusion O, guide wire 160 is re-advanced distally out of distal opening 356 of inner shaft 304 to perforate the intima I distal of occlusion and enter true lumen 204 distal of occlusion O, as shown in FIG. 15. Guide wire 160 may be the same guidewire used to guide catheter 300 into the subintimal tract T or may be a different guidewire. For example, and not by way of limitation, guidewire 160 may be removed and a second guidewire with a stiffer tip or other desirable feature for penetrating the intima I may be loaded into guidewire lumen 306 of catheter 300 and extended distally from distal opening 356. In another embodiment, guidewire 360 may be removed and another suitable tool, such as but not limited to a microcatheter or needle or stylet, may be loaded into guidewire lumen 306 and extended out of distal opening 356 to perforate the intima I and access true lumen 204 distal of occlusion O.

With guidewire 160 extending from outside of the patient into true lumen 202 proximal of occlusion O, into and within subintimal tract T, and out of subintimal tract T into true lumen 204 distal of occlusion O, the balloons are deflated and catheter 300 may be removed. Further steps for delivering a stent may be performed as described below with respect to FIGS. 16-18.

Figure 17:
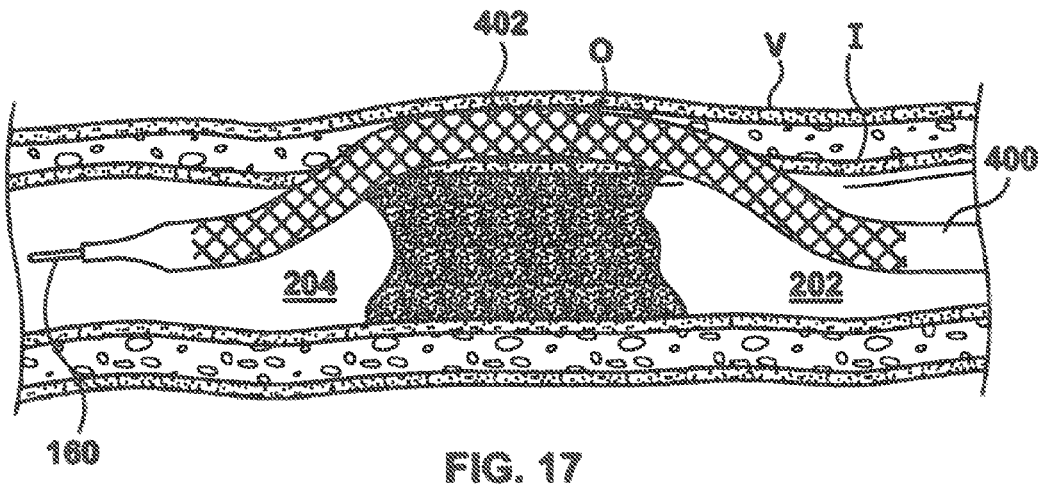
Figure 18:
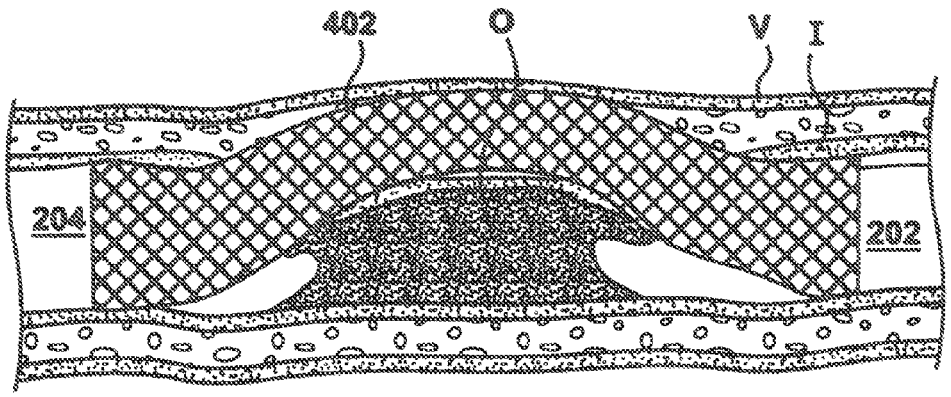

After catheter 100 or 300 has been removed, a covered or uncovered stent may be placed within the subintimal reentry conduit to facilitate flow from the lumen of the vessel upstream of occlusion O, through the subintimal tract T and back into the lumen of the vessel downstream of occlusion O. For example, FIG. 17 shows a distal end of a catheter 400 having a stent 402 mounted thereon being advanced over guidewire 160 to a position where a distal end of the radially collapsed stent 402 is in true lumen 204 of vessel V downstream of occlusion O, a proximal end of stent 402 is in true lumen 202 of vessel V upstream of occlusion O, and a midportion of stent 402 extends through the subintimal conduit. Stent 402 may then be deployed by either self-expansion or balloon inflation within the subintimal conduit to dilate the subintimal conduit and compress the adjacent occlusion O. Stent 402 provides a scaffold which maintains the subintimal conduit in an open condition capable of carrying blood downstream of occlusion O. Thereafter, guidewire 160 and catheter 400 may be removed from the patient, leaving stent 402 in an expanded configuration and creating a radially supported, subintimal blood flow channel around occlusion O as seen in FIG. 18. In some cases, it may be desirable to enlarge the diameter of the subintimal tract before or instead of advancing stent catheter 400 into and through it. Such enlargement of the subintimal tract may be accomplished by passing a balloon catheter over guidewire 160 and inflating the balloon to dilate the tract, or may be any other suitable tract enlarging, dilating or de-bulking instrument that may be passed over guidewire 160.

As described herein, catheter shafts such as outer shaft 102, 302 and inner shaft 104, 304, may be formed of a polymeric material, non-exhaustive examples of which include polyethylene, polyethylene block amide copolymer (PEBA), polyamide and/or combinations thereof, either laminated, blended or co-extruded. Optionally, such shafts or portions thereof may be formed as a composite having a reinforcement material incorporated within a polymeric body in order to enhance strength and/or flexibility. Suitable reinforcement layers include braiding, wire mesh layers, embedded axial wires, embedded helical or circumferential wires, hypotubes, and the like. In one embodiment, for example, at least a proximal portion of main outer shaft 102, 302 or inner shaft 104, 304 may be formed from a reinforced polymeric tube. Further, the balloons described herein may be formed of materials known to those skilled in the art. For example, and not by way of limitation, the balloons may be formed from PEBA, PET, PE, polyurethane, nylon, or blends thereof.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment.

What is claimed is:

1. A catheter for bypassing an occlusion via a subintimal approach, the catheter comprising:
    a catheter shaft including a guidewire lumen disposed therethrough, the catheter shaft having a shaft longitudinal axis;
    a first balloon coupled to an exterior of the catheter shaft, wherein a proximal portion of the first balloon is coupled to the catheter shaft at a first balloon proximal bond and a distal portion of the first balloon is coupled to the catheter shaft at a first balloon distal bond, wherein the first balloon is not coupled to the catheter shaft between the first balloon proximal bond and the first balloon distal bond, and wherein the catheter shaft is external to the first balloon between the first balloon proximal bond and the first balloon distal bond; and
    a second balloon coupled to an exterior of the catheter shaft opposite the first balloon relative to the catheter shaft, wherein a proximal portion of the second balloon is coupled to the catheter shaft at a second balloon proximal bond and a distal portion of the second balloon is coupled to the catheter shaft at a second balloon distal bond, wherein the second balloon is not coupled to the catheter shaft between the second balloon proximal bond and the second balloon distal bond, and wherein the catheter shaft is external to the second balloon between the second balloon proximal bond and the second balloon distal bond;
    wherein when the catheter is disposed in the subintima of a vessel and the first balloon and the second balloon are inflated, the catheter shaft bends such that a tip of the catheter shaft distal of the first and second balloons is oriented towards a true lumen of the vessel.

2. The catheter of claim 1, wherein when not disposed within the subintimal space, the shaft longitudinal axis, a longitudinal axis of the first balloon, and a longitudinal axis of the second balloon are substantially co-planar.

3. The catheter of claim 1, further comprising a guidewire extending through the guidewire lumen.

4. The catheter of claim 1, wherein the first balloon has an inflated outer diameter in the range of 1 mm to 3 mm.

5. The catheter of claim 4, wherein the second balloon has an inflated outer diameter in the range of 1 mm to 3 mm.

6. The catheter of claim 1, wherein the catheter shaft further includes an inflation lumen in communication with a first balloon interior of the first balloon and a second balloon interior of the second balloon.

7. A method of bypassing an occlusion in a true lumen of a vessel, the method comprising the steps of:
    advancing a catheter in the true lumen of the vessel proximal to the occlusion, into a subintimal space between layers of the vessel wall proximal to the occlusion, and within the subintimal space such that a distal end of the catheter is distal of the occlusion, wherein the catheter includes,
    a catheter shaft having a shaft longitudinal axis,
    a first balloon coupled to an exterior of the catheter shaft, wherein a proximal portion of the first balloon is coupled to the catheter shaft at a first balloon proximal bond and a distal portion of the first balloon is coupled to the catheter shaft at a first balloon distal bond, wherein the first balloon is not coupled to the catheter shaft between the first balloon proximal bond and the first balloon distal bond, and wherein the catheter shaft is external to the first balloon between the first balloon proximal bond and the first balloon distal bond, and
    a second balloon coupled to an exterior of the catheter shaft opposite the first balloon relative to the catheter shaft, wherein a proximal portion of the second balloon is coupled to the catheter shaft at a second balloon proximal bond and a distal portion of the second balloon is coupled to the catheter shaft at a second balloon distal bond, wherein the second balloon is not coupled to the catheter shaft between the second balloon proximal bond and the second balloon distal bond, and wherein the catheter shaft is external to the second balloon between the second balloon proximal bond and the second balloon distal bond, and
    inflating the first balloon and the second balloon such that the catheter shaft is bent and the distal tip of the catheter shaft is directed towards the true lumen distal of the occlusion.

8. The method of claim 7, wherein the first balloon and the second balloon are inflated simultaneously.

9. The method of claim 7, further comprising the steps of:
    prior to the step of advancing the catheter in the true lumen of the vessel, advancing a guidewire in the true lumen of the vessel proximal of the occlusion, into the subintimal space proximal to the occlusion, and within the subintimal space such that a distal end of the guidewire is distal of the occlusion;
    wherein the step of advancing the catheter in the true lumen proximal of the occlusion and into the subintimal space comprises advancing the catheter over the guidewire.

10. The method of claim 9, further comprising the step of retracting the guidewire prior to inflating the first balloon and the second balloon.

11. The method of claim 10, further comprising the step of advancing the guidewire through the catheter shaft after inflating the first balloon and the second balloon to puncture the intima and enter the true lumen distal of the occlusion.

12. The method of claim 11, further comprising the steps of:
    deflating the first balloon and the second balloon after the guidewire has entered the true lumen distal of the occlusion; and
    removing the catheter shaft from the vessel.

13. A catheter for bypassing an occlusion via a subintimal approach, the catheter comprising:
    a catheter shaft including a guidewire lumen disposed therethrough, the catheter shaft having a shaft longitudinal axis;
    a first balloon having a first balloon longitudinal axis and being coupled to an exterior of the catheter shaft, wherein a proximal portion of the first balloon is coupled to the catheter shaft at a first balloon proximal bond and a distal portion of the first balloon is coupled to the catheter shaft at a first balloon distal bond, wherein the first balloon is not coupled to the catheter shaft between the first balloon proximal bond and the first balloon distal bond, and wherein the catheter shaft is external to the first balloon between the first balloon proximal bond and the first balloon distal bond;

a second balloon having a second balloon longitudinal axis and being coupled to an exterior of the catheter shaft opposite the first balloon relative to the catheter shaft, wherein a proximal portion of the second balloon is coupled to the catheter shaft at a second balloon proximal bond and a distal portion of the second balloon is coupled to the catheter shaft at a second balloon distal bond, wherein the second balloon is not coupled to the catheter shaft between the second balloon proximal bond and the second balloon distal bond, and wherein the catheter shaft is external to the second balloon between the second balloon proximal bond and the second balloon distal bond; and a third balloon having a third balloon longitudinal axis and being coupled to an exterior of the catheter shaft along the third balloon, wherein the catheter shaft is external to the third balloon and the third balloon is disposed between the first balloon and the catheter shaft;

wherein when the first, second, and third balloons are uninflated and without external forces acting upon them, the first balloon longitudinal axis, the second balloon longitudinal axis, the third balloon longitudinal axis, and the shaft longitudinal axis are substantially aligned along a common plane.

14. The catheter of claim 13, wherein when the catheter is disposed in a subintimal space and the first balloon, the second balloon, and the third balloon are inflated, the third balloon and the catheter shaft rotate relative to the first balloon and the second balloon such that a distal end of the catheter shaft rotates.

15. The catheter of claim 14, wherein when the catheter shaft and the third balloon rotate, the first balloon longitudinal axis, the second balloon longitudinal axis, the third balloon longitudinal axis, and the shaft longitudinal axis are not generally aligned along a common plane.

16. The catheter of claim 15, wherein the first balloon has an inflated outer diameter in the range of 1 mm to 3 mm.

17. The catheter of claim 16, wherein the second balloon has an inflated outer diameter in the range of 1 mm to 3 mm.

18. The catheter of claim 17, wherein the third balloon has an inflated outer diameter in the range of 1 mm to 3 mm.

19. The catheter of claim 13, wherein the catheter shaft further includes an inflation lumen in communication with a first balloon interior of the first balloon, a second balloon interior of the second balloon, and a third balloon interior of the third balloon.

20. A method of bypassing an occlusion in a true lumen of a vessel, the method comprising the steps of:

advancing a catheter in the true lumen of the vessel proximal to the occlusion in the vessel, into a subintimal space between layers of the vessel wall proximal to the occlusion, and within the subintimal space such that a distal end of the catheter is distal of the occlusion, wherein the catheter includes, a catheter shaft having a shaft longitudinal axis, a first balloon coupled to an exterior of the catheter shaft, wherein a proximal portion of the first balloon is coupled to the catheter shaft at a first balloon proximal bond and a distal portion of the first balloon is coupled to the catheter shaft at a first balloon distal bond, wherein the first balloon is not coupled to the catheter shaft between the first balloon proximal bond and the first balloon distal bond, and wherein the catheter shaft is external to the first balloon between the first balloon proximal bond and the first balloon distal bond, a second balloon coupled to an exterior of the catheter shaft opposite the first balloon relative to the catheter shaft, wherein a proximal portion of the second balloon is coupled to the catheter shaft at a second balloon proximal bond and a distal portion of the second balloon is coupled to the catheter shaft at a second balloon distal bond, wherein the second balloon is not coupled to the catheter shaft between the second balloon proximal bond and the second balloon distal bond, and wherein the catheter shaft is external to the second balloon between the second balloon proximal bond and the second balloon distal bond, and a third balloon having a third balloon longitudinal axis and being coupled to an exterior of the catheter shaft along the third balloon, wherein the catheter shaft is external to the third balloon and the third balloon is disposed between the first balloon and the catheter shaft, and inflating the first balloon, the second balloon, and the third balloon such that a distal end of the catheter shaft is rotated to be directed towards the true lumen distal of the occlusion.

21. The method of claim 20, wherein the first balloon, the second balloon, and the third balloon are inflated simultaneously.

22. The method of claim 20, further comprising the steps of:

prior to the step of advancing the catheter in the true lumen of the vessel, advancing a guidewire in the true lumen of the vessel proximal to the occlusion in the vessel, into the subintimal space proximal to the occlusion, and within the subintimal space such that a distal end of the guidewire is distal of the occlusion;

wherein the step of advancing the catheter in the true lumen proximal of the occlusion and into the subintimal space comprises advancing the catheter over the guidewire.

23. The method of claim 22, further comprising the step of retracting the guidewire prior to inflating the first balloon, the second balloon, and the third balloon.

24. The method of claim 23, further comprising the step of advancing the guidewire through the catheter shaft after inflating the first balloon, the second balloon and the third balloon to puncture the intima and enter the true lumen distal of the occlusion.

25. The method of claim 24, further comprising the steps of:

deflating the first balloon, the second balloon and the third balloon after the guidewire has entered the true lumen distal of the occlusion; and removing the catheter shaft from the vessel.

* * * * *